United States Patent [19]

Hombrouckx

[11] Patent Number: 5,120,303
[45] Date of Patent: Jun. 9, 1992

[54] METHOD AND APPARATUS FOR HEMODIALYSIS WITH A SINGLE NEEDLE

[76] Inventor: Remi O. J. Hombrouckx, Hogerluchtstraat, 6, 9600 Ronse, Belgium

[21] Appl. No.: 359,665
[22] PCT Filed: Sep. 10, 1987
[86] PCT No.: PCT/BE87/00013
§ 371 Date: Apr. 28, 1989
§ 102(e) Date: Apr. 28, 1989
[87] PCT Pub. No.: WO88/01880
PCT Pub. Date: Mar. 24, 1988

[30] Foreign Application Priority Data

Sep. 10, 1986 [BE] Belgium ............... 217142
Oct. 17, 1986 [BE] Belgium ............... 217301

[51] Int. Cl.$^5$ ............... A61M 1/03
[52] U.S. Cl. ............... 604/4; 604/5; 604/51
[58] Field of Search ............... 604/4–6, 604/905, 27–31, 51; 128/DIG. 13

[56] References Cited

U.S. PATENT DOCUMENTS

| | | | |
|---|---|---|---|
| 4,235,231 | 11/1980 | Schindler et al. | 604/4 |
| 4,490,135 | 12/1984 | Troutner | 128/DIG. 13 X |
| 4,643,714 | 2/1987 | Brose | 604/4 |
| 4,650,457 | 3/1987 | Morioka et al. | 604/4 |
| 4,776,837 | 10/1988 | Kopp | 604/4 |
| 4,828,543 | 5/1989 | Weiss et al. | 604/4 |
| 4,867,739 | 9/1989 | Kawano | 604/4 |

FOREIGN PATENT DOCUMENTS 333574 12/1984 Fed. Rep. of Germany ........ 604/29
3600793 7/1987 Fed. Rep. of Germany ........ 604/29

Primary Examiner—Robert A. Hafer
Assistant Examiner—Kerry Owens
Attorney, Agent, or Firm—Sughrue, Mion, Zinn, Macpeak & Seas

[57] ABSTRACT

The dialysis apparatus with a single needle comprises a reversible pump (3) controlled by a program so as to provide, in the first rotation direction, for the removal of a predetermined blood volume outside the circulatory system of a patient (P), the treatment of said blood volume in an artificial kidney (4) and the discharge into an expansion chamber (5), as well as, in a reverse rotation direction, to provide for the return of purified blood towards the patient (P) after a second purification in the artificial kidney (1). The expansion chamber (5) under pressure is used both as a blood accumulation container and as a housing for measuring the pressure. Its capacity is 4 to 5 times more than the internal volume of the artificial kidney (4).

10 Claims, 5 Drawing Sheets

METHOD AND APPARATUS FOR HEMODIALYSIS WITH A SINGLE NEEDLE

The present invention relates to a method and apparatus for hemodialysis using a single needle, in which a predetermined volume of blood from a fistula, a vein or an artery is alternately drawn from the body of the patient to be filtered in an artificial kidney and then is returned to the patient at the same puncture location using a single, same needle.

The dialysis equipment comprises:
a needle or a catheter;
a tube between the needle and the segment of a pump;
a pump, preferably a peristaltic pump;
a low compliance, compact artificial kidney, for example an artificial kidney will hollow fibers;
an expansion chamber composed of a closed receptacle provided with a blood delivery and removal tube and provided in its upper part with an apical air tube intended for use as a pressure line and provided, a few millimeters lower, with an infusion line enabling the kidney to be rinsed, medication to be administered and the height of the blood level to be adjusted by means of air under pressure;
a pressure line which connects the expansion chamber to a compliance chamber so as to absorb the periodic fluctuations in pressure produced by the varied filling of the expansion chamber;
a device for pressure measurement, enabling the pressure to be taken in the expansion chamber, the compliance chamber or the pressure line;
an apparatus for measuring and control; and
safety devices.

Hemodialysis is principally used in nephrology to treat acute as well as chronic renal inadequacies. This treatment consists of removing toxic substances from the blood in an external circuit using an artificial kidney based on the principle of the diffusion of the toxic substances through a semi-permeable membrane.

Patients must be connected two to three times per week to a semi-automatic artificial kidney at intervals generally of between two to three days on average. They remain connected to an artificial kidney for several hours by means of a shunt-needle or catheter and tubes in a synthetic material.

In conventional dialysis the blood flows in a given direction from side to side of an artificial kidney, that is from an arterial side to a venous side. The blood is removed from the circulatory system of the patient on the arterial side, through the catheter or through the dialysis needle, then driven by means of a pump in a determined direction in the artificial kidney, and ends up in an expansion vessel in which the pressure is recorded and the air bubbles collected, then to be returned into the circulatory system of the patient, in accordance with the following methods: if it is a two-needle system, the purified blood is returned at once through a second catheter or needle connected to the venous side, or, if it is a single puncture system, the purified blood is returned through a second pump or through a system of valves, to the first needle which is Y-shaped.

The first single-needle system is described by Kopp et al in an article entitled "Single needle dialysis"[and published in "Trans. Am. Soc. Art. Intern. Organs" No. 18, pages 75–80, 1972.

This system is the object of U.S. Pat. No. Re. 29,346 and U.S. Pat. No. 3,830,234.

The problem posed consists of drawing off and returning the blood to the same location. This implies technical difficulties with regard to the recirculation of the filtered blood, but has the incontestable advantage that it merely requires the introduction of a single needle.

This system contains a single pump segment and two solenoid valves on the arterial and venous blood line.

The valves are articulated in turn.

The blood is pumped from the circulator system of the patient, in particular from an artery, until a predetermined pressure is reached in the venous chamber. Once this pressure is reached, the arterial line is blocked and the venous line is opened.

The pump turns continuously in the same direction. In this manner, the blood is returned through the same needle at the same location into the circulatory system of the patient.

Due to the fact that the cycle is regulated by the fact of achieving a certain pressure and then by the passage of a certain time, this regulation is generally designated as the pressure-time system using a single needle. In 1979, Ahmad proposed a modification, by causing the valves to open and close for determined periods of time. He considered it useful to include three compressible pads of 10 ml each in the arterial circulatory system. A blood flow of 200 to 300 ml/min and a 5 second closing time were optimal. In addition to the advantage of a single puncture, this system maintained natural venous pressure during the replacement of the blood.

Since the pump operates without interruption, reduced pressure is obtained in the arterial line between the pump and the valve if the arterial line is closed. Increased recirculation is therefore as well as a danger of drawing air into the tubes. This causes the formation of foam in the venous chamber, which causes the coagulation of the blood in this chamber.

As a disadvantage, excessive ultrafiltration is noted when it is sought to maintain the flow at a sufficiently high level.

This pressure-time system can be used only rarely in a patient having a fistula in the groin and suffering from hypertension, due to the natural pressure in the fistula which is too high.

A very practical method of dialysis is single-needle pressure-pressure hemodialysis. It has been described since 1973 by Professor Dr. S. Ringoir and his colleagues in a publication entitled "New pump system for one needle hemodialysis", published by EDTA Abstracts, Vienna 200, 1973.

It also uses a system with a single needle in which the delivery of blood to the extracorporeal circuit is carried out using a double head pump (Bellco 760 B). The activity of the pumps, which are switched on alternately, resides on a pressure-pressure control.

During the arterial phase, venous blood is removed from the body of the patient, by means of an arterial pump, and taken to a venous expansion chamber, which is intended to produce a determined accumulation of blood. The arterial phase is continued until a recommended pressure is reached in the venous chamber. The arterial pump is stopped and blocked as is the arterial line. The venous pump immediately begins operating and returns the blood to the circulatory system of the patient through the same needle until a recommended minimum pressure is reached. This pressure regulation depends, among other things, on the degree of ultrafiltration which it is sought to obtain. An alternative on this method consists of comparing the recommended pressures with the pressures in the arterial chamber, as is described for example in U.S. Pat. No. 4,643,714.

This system has been improved by Dr. R. Hombrouckx et al by the insertion of an arterial expansion chamber between the arterial pump and the dialyzer.

Since the use of artificial kidneys with hollow fibers, which have low compliance, the arterial expansion chamber has provided the following considerable advantages:

1. easy connection of the patient to the dialysis equipment since a single puncture is necessary;
2. continuous flow with a consequent better dialysis;
3. prevention of the formation of foam, due to the fact that, during the venous phase, the blood is not drawn off through the kidney but rather returned through the kidney, due to the intervention of the arterial expansion chamber under pressure;
4. removal of foam due to the fact that the blood removal tube is provided below;
5. reduction of recirculation; although the loss through recirculation is still always 10%;
6. adjustment of the flow through the reduction of the number of starts and stoppages of the pumps and, therefore, reduction in the "dead times" between the stoppage of one of the pumps and the start-up of the other one;
7. fully adjustable ultrafiltration, both minimum and maximum;
8. possibility of use with all the fistulas, including those with high natural pressure, such as the fistulas in the groin and the "Safena" vein at the top of the forearm.

The most important disadvantage of single-needle pressure-pressure hemodialysis resides in the complexity of the equipment, such that home dialysis remains laborious.

These two pumps require a complex, sensitive control system based on the creation of a determined pressure. The variability and the severe precision of the recommended operating program renders difficult the carrying out of home dialysis by close family members of the patient. The handling of known dialysis equipment requires several months of training.

The present invention is therefore to produce a simpler apparatus for carrying out dialysis.

As characterized in the attached claims, the removal of a predetermined quantity of blood from the body of the patient and the movement through the artificial kidney in the expansion chamber on the one hand, and the return of the filtered blood into the body of the patient on the other hand, by movement of the blood in the opposite direction along one same blood line, using a reversible pump, the direction of rotation of which is controlled automatically in a programmed manner using a regulating and measuring device. Said regulating and measuring device is for example a device for measuring the pressure, the flow, the time or the volume.

This artificial kidney is connected on one side by means of a pump and a single needle or catheter to the circulatory system of the patient and on the other side connected to an expansion chamber containing blood delivery and removal tubes and, in the upper part, an apical air tube intended to act as a pressure line and, a few millimeters lower, an infusion line for rinsing the kidney, administering medication and adjusting the level of the blood by means of the amount of air injected.

The fluctuations in pressure in the expansion chamber and the compliance chamber are detected by a device for measuring pressure.

By using a single pump and by removing occlusive valves and superfluous measuring and regulating equipment the cost of the equipment and the number of coupling components in the blood line of the dialysis equipment have been substantially reduced.

Assembly, disassembly, cleaning, maintenance and checking of the dialysis equipment is thus substantially simplified. The simplicity of the alternating operation renders easy the use of the equipment.

Since the internal contents of the blood line, the pump segment, the artificial kidney and the expansion chamber are very reduced, the assembly arrangement of the dialysis equipment in accordance with the invention can be considered as being very safe.

In the case of a very serious problem, the pump is stopped, which immediately stops the supply of blood.

Due to this fact, the contents of the artificial kidney and the instantaneous contents of the expansion chamber can be lost in the worst of cases. Even then, the system is considered as safe because these contents are at most 200 ml of blood.

Due to the fact that the blood goes through the artificial kidney twice in a row, a net increase is noted in the effectiveness of the dialysis.

Leaving the puncture point, the pump and the artificial kidney, the blood line goes to the expansion chamber, which is connected by a pressure tube to a compliance chamber, so as to attenuate the fluctuations in pressure caused by the variable amount of blood in the expansion chamber. These fluctuations are measured by a device for measuring the pressure with adjustable recommended values, which serves in turn to modify the direction of rotation of the pump and, therefore, the direction of circulation of the blood in the blood line.

In accordance with an alternative of the method in accordance with the invention, the delivery of a predetermined amount of blood coming from the circulatory system of the patient as well as the movement through the artificial kidney to an expansion chamber is carried out with a first pump head, while the return of the filtered blood to the circulatory system is carried out, after a second filtering through the artificial kidney, in the opposite direction using a second pump, which is set off alternately, with the regulation of the alternate operation of the double pump residing, as is known, on pressure-pressure regulation.

This alternative embodiment has the advantage of preventing any recirculation of the quantity of blood trapped in the pump segment and in the blood lines between the needle and the pump on the one hand and the pump and the artificial kidney on the other hand, such that no amount of untreated blood is returned to the circulatory system of the patient, whatever the length and cross-section of the blood lines and the pump segment.

The withdrawn blood is preferably returned by mean of the first pump to the artificial kidney and from there to the expansion chamber, which is intended to accumulate a determined amount of blood under pressure. This first phase is continued until a previously selected pressure is reached in the expansion chamber.

In a second phase, a second pump pumps the blood from the expansion chamber to the artificial kidney and, through the same needle, to the circulatory system of the patient.

These particular features and details of the invention, as well as others, will become apparent from the following detailed description of three different embodiments of the invention, with reference to the following drawings, which illustrate them schematically.

In these drawings.

In these drawings, the same reference numerals designate identical or similar components.

Figure 1:
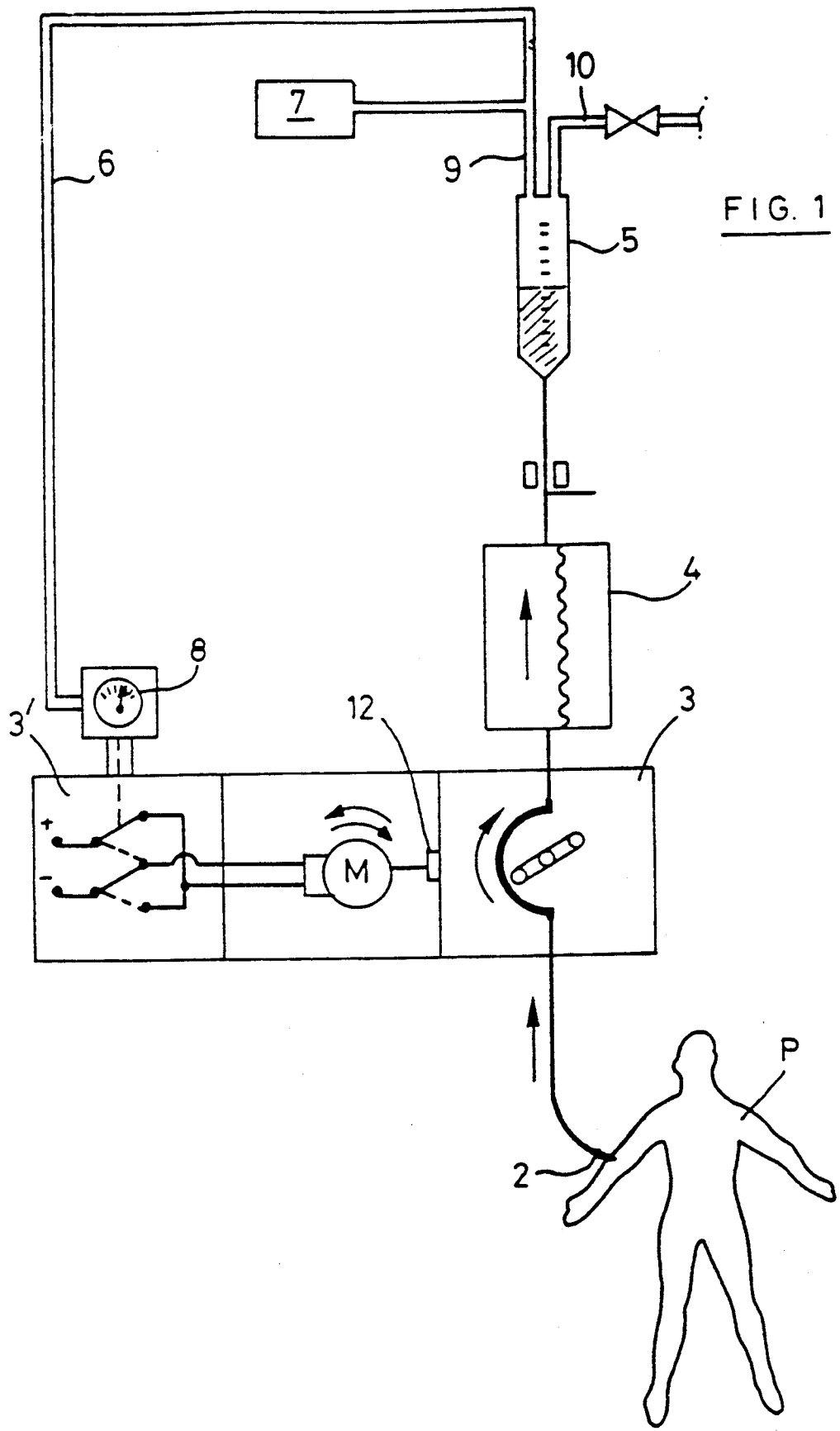
FIG. 1 is a schematic illustration of one arrangement of the first embodiment of the dialysis equipment in accordance with the invention; the arrows indicate the direction of the arterial blood during the arterial phase.
Figure 2:
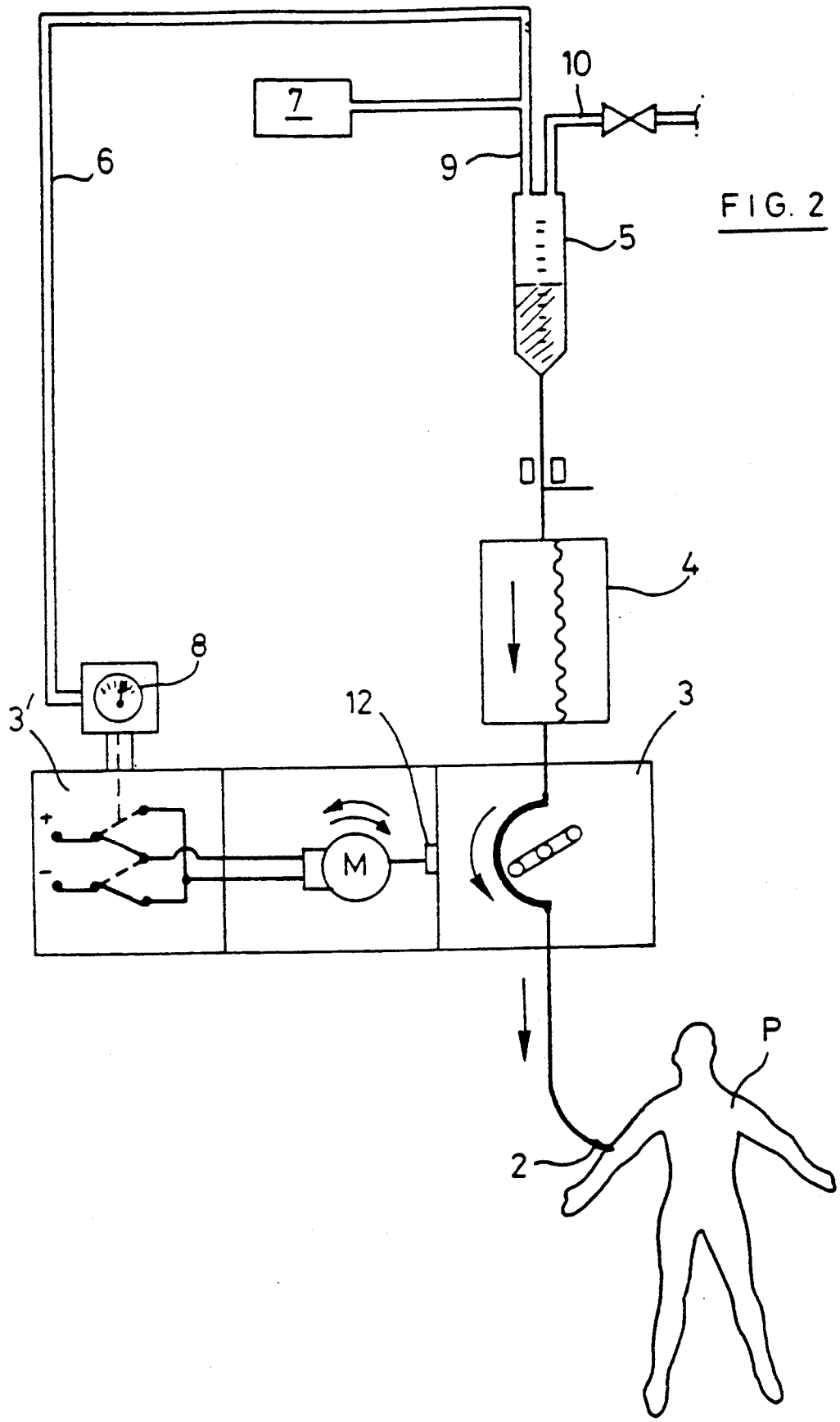
FIG. 2 illustrates the operation of the apparatus illustrated in FIG. 1, during the venous phase.
Figure 3:
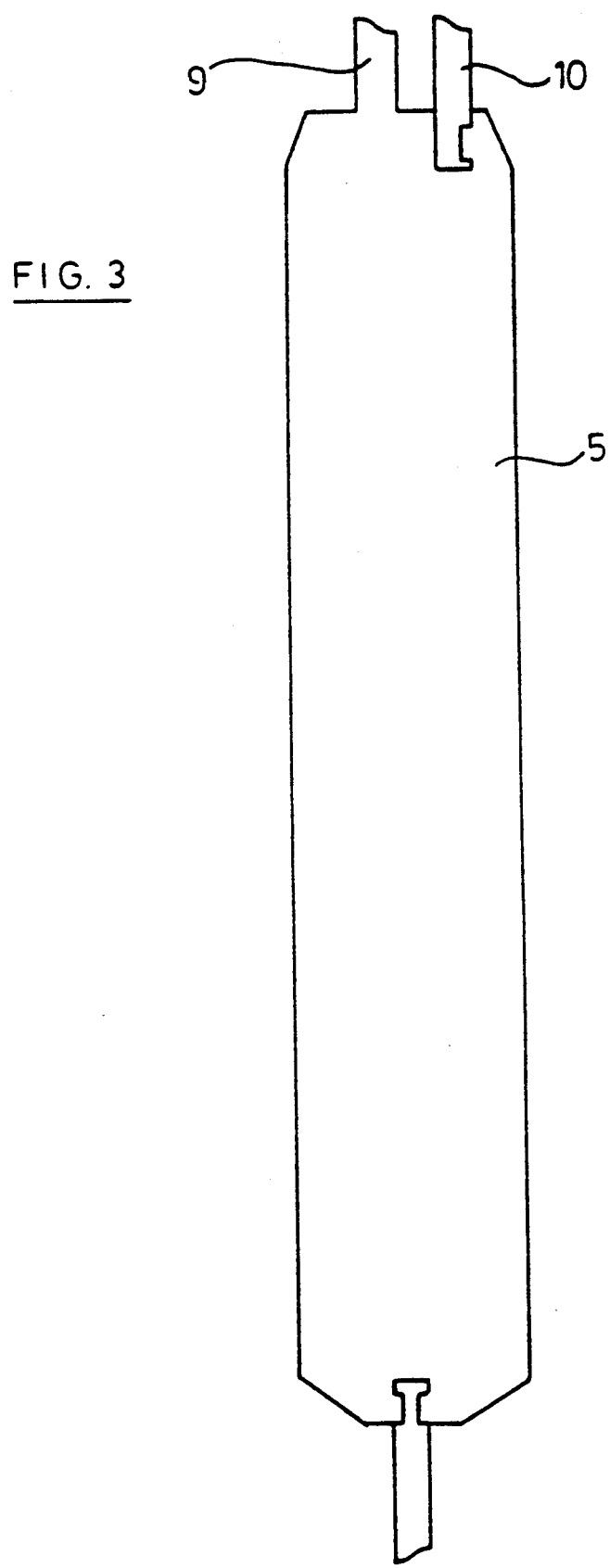
FIG. 3 is a vertical cross-section of an expansion chamber including a removal base.
Figure 4:
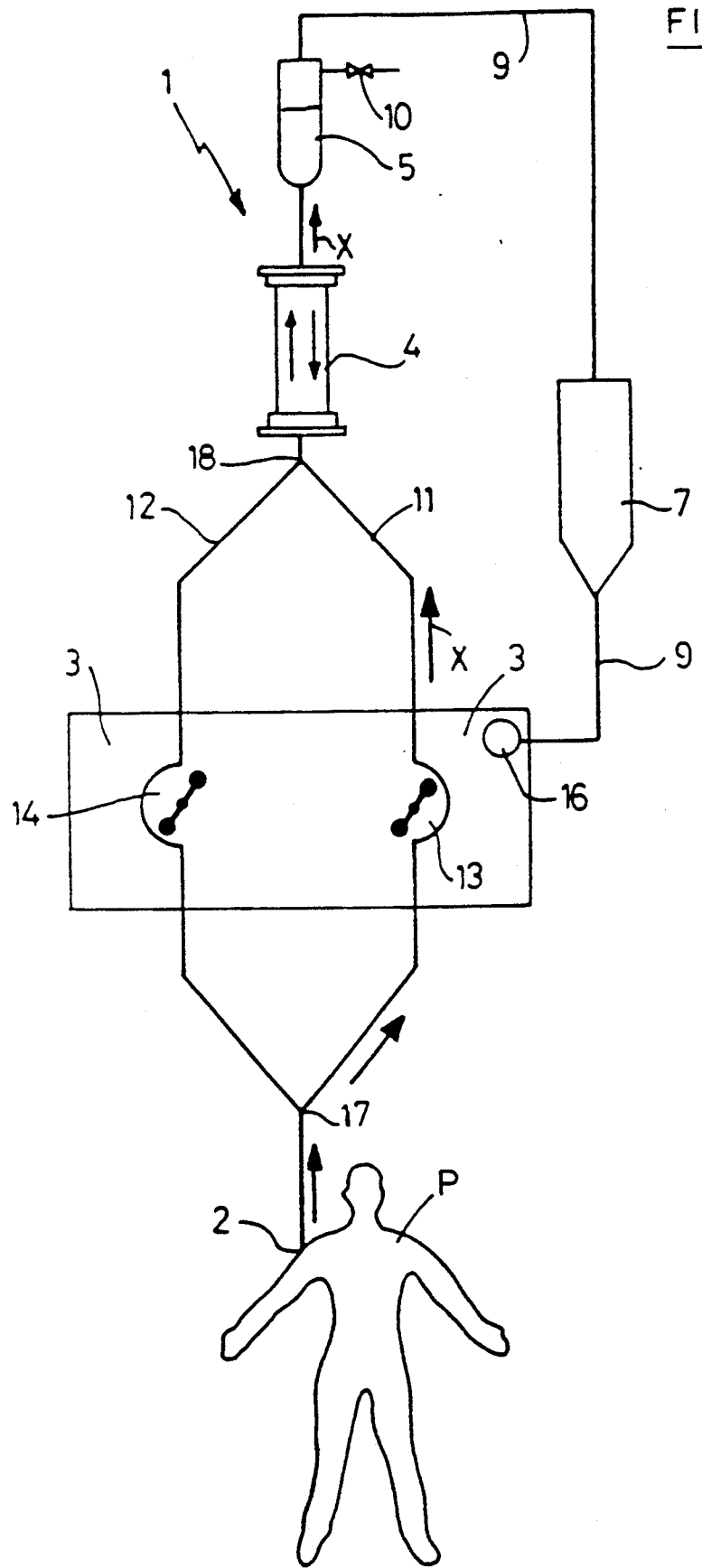
FIGS. 4 and 5 illustrate an alternative embodiment of the dialysis equipment in accordance with the invention.
Figure 5:
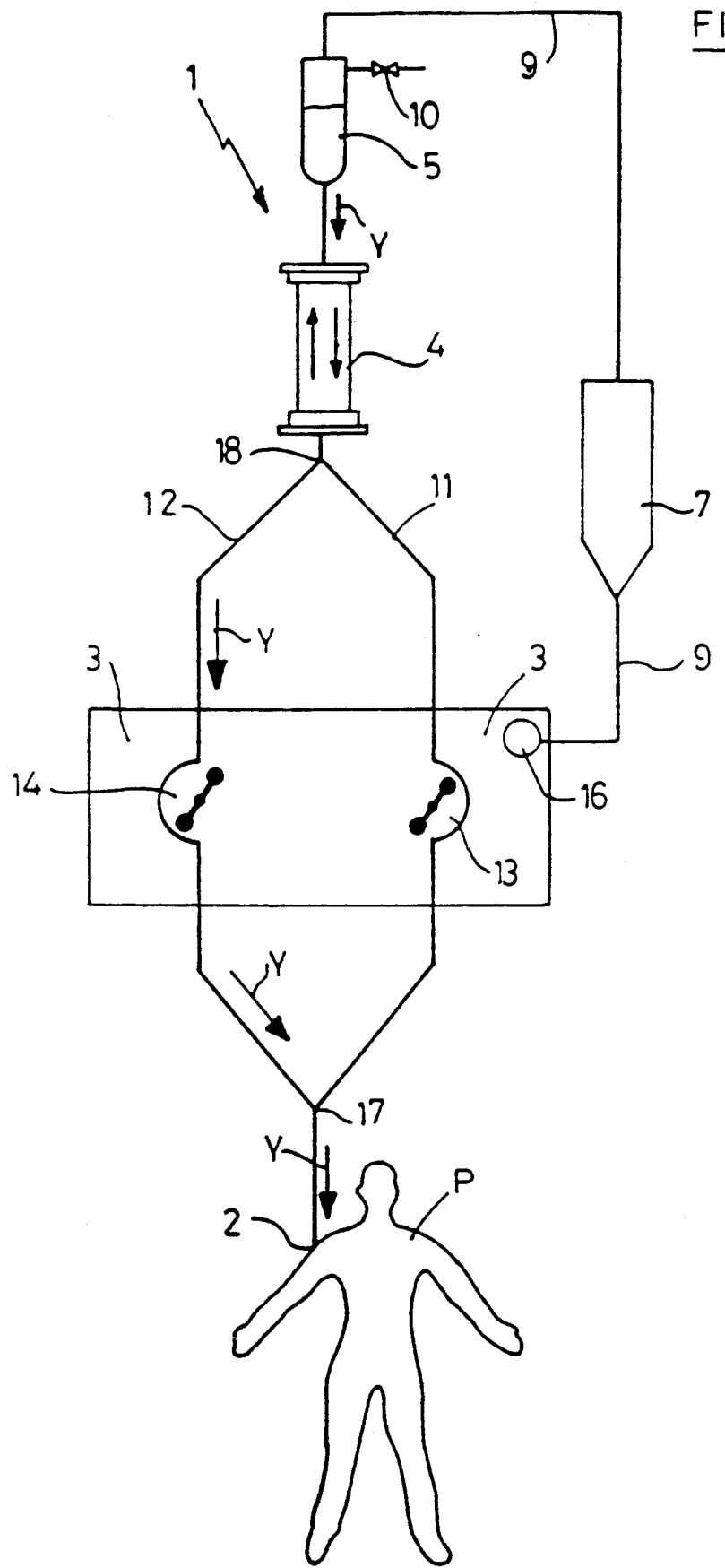

As illustrated in FIG. 1, the dialysis equipment, designated overall by the reference numeral 1, comprises:

- a needle 2 of the Deseret Angiocath 14 GA ¼ type;
- a suitable blood line of the BL 174 type mounted between the above-mentioned needle 2 and the pump mentioned below;
- a pump 3 of the BL 760 N or BL 705—transformed into a reversible direction pump or a Watson Marlow type 502 pump with a transformed head and a device for the reversal of the direction of rotation 3';
- an low volume artificial kidney 4, for example an artificial kidney with hollow fibers;
- an arterial expansion chamber 5 acting as the reservoir under pressure for the accumulation of blood;
- a pressure line of the BL 374+BL 409 type with a large capacity chamber for the air and including a compliance chamber;
- a manometer 8 for controlling the direction of rotation and the operation of the pump, of the Novo Sara type with maximum and minimum recommended values.

The arterial expansion chamber 5 (AEC) contains a cylindrical chamber ending beneath a conical base terminating in the tube connecting said chamber to the artificial kidney 4, and ending at the top in two air lines 9 and 10, one of which is apical and the other 10 implanted slightly lower; the upper line is a pressure line and the lower line is an infusion line 10 used for the rinsing of the kidney, the administration of medication, and adjustment of the blood level by means of the injection of air.

In a preferred embodiment, the chamber has a diameter of 35 mm and a height of 20 cm. It is generally made of rigid PVC or another biocompatible, non-deformable, rigid, transparent material.

The blood flows through the approximately 10,000 capillaries. This regeneration liquid winds in the opposite direction through the plastic sheath and rinses the fine tubes, the walls of which act as semi-permeable membranes.

This embodiment has the advantage of a minimal volume of blood, low pressure loss and maximum efficiency.

The blood flows out of the artificial kidney 4 through the lower part of the arterial expansion chamber 5.

The arterial phase continues and the blood is accumulated in the arterial expansion chamber 5 until the volume is 4 to 5 times greater than the contents of the artificial kidney 4 and the arterial blood line 3, which is approximately 150 ml.

The volume extension capacity varying under pressure, which is necessary to accumulate the blood, is obtained by the fact of compressing air in the upper part of the expansion chamber, in an air reservoir of approximately 650 to 2000 ml, designated by the name compliance chamber 7, which is assimilated with the pressure line 6.

When the control of the bidirectional pump is carried out by a pressure mechanism, the pressure is recorded in the expansion chamber above the artificial kidney; at minimum and maximum recommended pressure values in this mechanism, the pump changes direction and completes or begins the cycle.

A maximum recommended pressure value is introduced only at the moment when the arterial expansion chamber 5 is at a few centimeters from being completely full and the blood pump is reversed; the chamber 5 is then emptied from below; when it is almost completely empty, the minimum recommended pressure value is introduced and the pump 3 is reversed again so as to start the cycle again.

This arterial chamber 5 is filled and emptied therefore through the single orifice provided in the conical base.

As soon as a previously selected maximum pressure is reached, the blood is expelled from the expansion chamber 5 to the artificial kidney 4, flows a second time through the artificial kidney 4 and is returned in the opposite direction under the action of the same pump to the same blood line in the body of the patient.

The venous return phase is continued until the pressure in the above-identified expansion chamber 5 falls beneath a minimum pressure.

The compliance chamber which is mounted in the pressure line 7 is necessary to enable a sufficient accumulation of blood in the expansion chamber 5, without the delivery and the removal of blood causing great differences in pressure on the manometer 8; this would create serious problems in the fluctuations of pressure, which are negative for the adjustment of the ultrafiltration through the artificial kidney, since the movement of water through an artificial kidney 4 depends, in effect, on the pressure of the exchange membrane, which itself is dependent on the pressure in the blood compartment of the artificial kidney. Fluctuations in said compartment cause uncontrollable ultrafiltration phenomena. These phenomena are prevented with a compliance chamber of sufficient size to enable the fluctuations in pressure between the minimum and maximum filling of the expansion chamber 5 to be minimal; thus, it is possible to obtain:

homogeneous ultrafiltration; and great variability in the designation of preprogrammed pressures, since the pressure scale is not taken up by a determined recommended pressure, but only by a fraction.

The compliance chamber 7 can be any type of rigid chamber with a capacity of approximately 650 ml to 2000 ml with any shape. It can be inserted in the pressure line or can be mounted before the manometer in the pump. It must by necessity be located between the blood level of the expansion chamber 5 and the manometer 8; a bacterial filter is mounted in the pressure line 9 between the arterial expansion chamber 5 and the compliance chamber 7.

An alternative method for controlling the pump is the volumetric method: by providing for example ultrasound detection at the height of the expansion chamber, the pump can be made to change direction at minimum and maximum values of the amount of filling. This can be provided as a safety measure (that is, control of the pump is carried out by pressure, but at the same time a volume measurement (minimum and maximum) is carried at the height of the expansion chamber, so as to be able to correct possible erroneous pressure measurements). One disadvantage of this method of regulation by volume consists of not knowing under what pressure the dialysis is being carried out, and it is precisely this pressure which is important for the ultrafiltration. In a pressure-controlled pump, this ultrafiltration is directly proportional to the recommended pressure value.

This defect can possibly be corrected in a volumetrically controlled pump by allowing the ultrafiltration to take place through operation under a constant pressure difference in the blood compartment, provided the ultrafiltration is regulated by an ultrafiltration pump provided in the dialyzate compartment. In the most modern hemodialysis equipment, the ultrafiltration control unit is already incorporated.

A third possibility for regulating a pump consists of working with a timer control, by providing a first determined period of time for the arterial phase of the cycle and a second determined period of time for the venous phase of the cycle. This system has the disadvantage of creating irregular volume beats since the blood is not always present with sufficient availability, for example due to a slight obstruction in the blood supply. This type of control could cause problems of under- for over-filling of the expansion chamber, which could be corrected by a simultaneous volume check. In principle, it should be possible to control the pump by a time-dependent control means.

The most important advantage of bidirectional, single-needle hemodialysis resides in the fact that the blood flows twice through the artificial kidney 4. This blood is therefore better purified and filtered than in the known unidirectional systems. The effectiveness of the artificial kidney is approximately doubled in relation to other methods of dialysis, at least for certain molecules which are difficult to dialyze.

During the first passage through the artificial kidney, only the substances with low molecular weights are removed for the most part, a second passage enables better removal of substances with medium molecular weights than do conventional unidirectional systems.

A second advantage is a simplification in construction and control.

A great disadvantage of this single-needle hemodialysis is the recirculation of unfiltered blood into the circulatory system of the patient.

The recirculation decrease when the length and the contents of the blood lines and the artificial kidney are decreased. This method requires compact artificial kidneys, pump segments and blood lines.

An arterial expansion chamber prevents the formation of foam and provides a continuous flow direct from the artificial kidney. It is assumed that in the method of diffusion or hemodialysis, the variable flow improves the work of the artificial kidney by modifying the limit layers at the exchange surface of the membrane.

In the assembly shown in FIG. 1, the hemodialysis equipment comprises the following safety devices:
1. two air detectors 12: the first one mounted between the peristaltic pump 3 and the needle 2 and the second one mounted between the arterial expansion chamber and the peristaltic pump 3;
2. two devices for checking the number of rotations carried out by the pump 3: one for each direction of rotation of the pump; and
3. a detector for overpressure and underpressure, mounted between the needle 2 and the pump 3.

As safety devices, the following can also be provided: apparatus for measuring the capacity level as well as sonic, ultrasonic or photoelectric cell detectors.

Pump 3 can be composed:
of a peristaltic pump with rollers;
of a vacuum pump using unidirectional valves by means of which a continuous flow of blood can be obtained by the alternating movement of a piston;
of a membrane pump or a resilient blower.

It is obvious that the expansion chamber must be rigid in the case of a pump or a blood return mechanism using pressure, since the exact pressure must be able to be measured, without the intervention of other factors such as the elasticity of the receptacle in which the blood is accumulated. In the case of a pump or a blood return mechanism using volume or a period of time, a non-rigid structure, such as a balloon, can be used.

The assembly described above can be improved by branching the blood line and joining it to a second pump.

In this manner, a less satisfactory catheter or fistula flow can be overcome under certain conditions.

The dialysis equipment, bearing the overall reference numeral 1, comprises a double extracorporeal blood line 11, 12 containing a double-headed pump 13, 14, an artificial kidney 4 and an expansion chamber 5 under pressure.

The removal of the blood from the circulatory system of the patient P is carried out using a needle 2 of the Deseret Angiocath 14 GA ¼ type.

A first Y-shaped branch 17 is provided at the free end of the needle 2 to connect the needle 2 by means of a double blood line 11, 12 of the DL 174 type, to the double-headed pump 13, 14, for example of the Bellco 760 B type.

The double-headed pump 13, 14 is connected to the artificial kidney by means of a second Y-shaped component 18, which is mounted just at the entry of the artificial kidney.

The artificial kidney preferably has a smaller capacity.

The arterial expansion chamber is mounted behind the artificial kidney 4.

The pressure line is of the BL 374 or BL 049 type. It connects the arterial expansion chamber 5 to the compliance chamber 7 and to a manometer 16 which controls the double-headed pump.

The manometer 16 is for example of the Nuove Sara type with maximum and minimum recommended values.

The arterial expansion chamber 5 (AEC) is of the same type as that described above. It is formed by a cylindrical reservoir of approximately 200 ml, ending conically at the bottom in a blood line leading to the artificial kidney.

The pressure line is located above, while the infusion line is situated slightly below and is used for various purposes.

During the first phase, the blood is removed, by means of the first pump 13 and needle 2, from the circulatory system of the patient P and taken by a multitude of capillaries of the hollow fiber artificial kidney 4 in the direction of the arrow X to the expansion chamber 5.

The pressure in the expansion chamber 5 is selectively regulated. This pressure determines the operating pressure in the artificial kidney 4 and, consequently, the ultrafiltration.

The first phase is continued until a previously selected recommended pressure is reached in the expansion chamber 5. The increase in pressure is the consequence of the compression of the air due to the filling with blood of the expansion chamber.

This manometer 16 controls the double-headed pump 13, 14 and supervises the alternating operation thereof as in the already known system of the double-headed pump of Van Waeleghem and Ringoir. As soon as the expansion chamber 5 is filled to an appropriate level and the maximum pressure is reached, the first pump 3 is disarticulated and thus blocks the arterial blood line.

The second pump 14 is immediately started up. It is directed in an opposite direction to that of the first pump 13 and during the second phase pumps the blood out of the expansion chamber 5, through the artificial kidney 4 and along the two branches 17, 18 and the needle 2 into the circulatory system of the patient P. The second phase is continued until the pressure in the expansion chamber 5 goes below a previously selected minimum recommended pressure.

During the complete cycle, the blood flows twice in succession, in the opposite direction, through the artificial kidney In this second embodiment, the most important advantage of bidirectional, single-needle hemodialysis is maintained. This consists of passing the blood twice through the artificial kidney.

This provides better filtering of the blood and increased efficiency of the equipment.

An additional advantage of the second embodiment as compared to the first embodiment resides in the fact that recirculation, during each flow reversal in the blood line 11, 12 and the pump segments between needle 2 and the artificial kidney 4, is eliminated due to the insertion of a second pump and due to the splitting of the blood line into two branches 11, 12.

The simplicity of the equipment 1 is lost in part. However, recirculation, which constitutes the principal disadvantage of the above-identified bidirectional, single-needle hemodialysis system, is completely eliminated.

Recirculation can be ignored no matter what the length and the contents of the blood lines 11, 12 in the pump segments are.

The advantages provided by the arterial expansion chamber 5 in the Dr. Ringoir type single-needle, pressure-pressure type hemodialysis system are retained in both the first and second embodiments.

The arterial expansion chamber 5 forms a reservoir intended to provide the accumulation of blood between each flow reversal. It serves to record the pressure which controls the alternating operation of the double pump 13, 14.

This chamber is directly mounted onto the artificial kidney 4 instead of being integrated into the blood line. The connection of the chamber 5 and the artificial kidney is also sometimes made using as short a segment a possible.

The alternating operation of the dialysis equipment is obtained by means of a simple control program which enables close family to carry out the dialysis.

This system is particularly suitable for children, and also for adults who experience the difficulties of insufficient blood flow through the needle or the fistula.

For the return device, a double-head pump or a valve system in accordance with Kopp, as described in U.S. Pat. No. 4,643,714, can be used.

To increase the effectiveness of the dialysis, the operating conditions can be modified on the dialyzate side in the following manner:

1. accelerate the flow of dialyzate in the artificial kidney, by reducing the dimensions of the compartment of the artificial kidney intended for the dialyzate or by increasing the dialysis flow up to 750 to 1000 ml/min;
2. provide for each blood flow reversal in the artificial kidney, a simultaneous invention of the dialyzate flow using a device of the invention.

A preferred reversal device contains dialyzate supply and removal tubes arranged parallel with one another and divided in such a way that a single valve can block a pair of right tubes and a pair of left tubes. By making these valves dependent on those which regulate the flow of blood, it can be ensured that the blood flow and the dialyzate flow are always parallel or opposite. A particular type of flow can even be selected so to enable the filtration work of the kidney to select either low molecular weight substances or higher molecular weight substances.

It is obvious that the invention is not limited to the embodiment described above and that numerous modifications can be made thereto without departing from the framework of the invention.

Thus, the hemodialysis method and apparatus in accordance with the invention can easily be applied to hemofiltration.

I claim:

1. A method for hemodialysis using a single needle (2), comprising the steps of: alternately removing, from the body of a patient (P) by means of a pump (3), a predetermined volume of blood coming from a fistula, a vein or an artery: and filtering the removed volume of blood in an artificial kidney (4) and then returning it to the patient (P) at the same puncture location by a single and same needle; wherein the removal of the predetermined volume of blood from the body of the patient and the movement of the blood in a first direction (X) through the artificial kidney to an expansion chamber on the one hand, and the return of the filtered blood into the body of the patient, on the other hand, by movement of the blood in an opposite direction (Y) through a single and same blood line (6) and the same needle, are carried out using a reversible pump, the direction of rotation of which is controlled automatically in a programmed manner by means of a regulating and measuring device, and wherein the filtration of the blood is carried out twice in succession in the artificial kidney (4), that is a first time during a blood delivery phase in the first direction (X) and during a blood return phase in the second direction (Y) which is opposite to said first direction (X).

2. The method in accordance with claim 1, wherein the removal of a predetermined volume of blood and the movement of the blood through the artificial kidney in the expansion chamber on the one hand, is carried out by a first pump (13) in direction (X) while the return of the filtered blood into the body of the patient on the other hand, by movement in the opposite direction (Y) though a single and same blood line (6) and the same needle, is carried out by means of a second pump (14), with the two pumps being started up automatically in succession in a programmed manner under the control of a measuring and regulating device.

3. The method in accordance with claim 1, wherein the delivery of the blood into the expansion chamber (5) which is provided at the end of the above-identified blood line and the return of the blood from the expansion chamber (5) to the artificial kidney (4) is carried out through the same orifice at the bottom of the expansion chamber (5).

4. The method in accordance with claim 2, wherein the pumps (13, 14) are started up in turn.

5. The method in accordance with claim 4, herein the two pumps (13, 14) are controlled automatically and in a programmed manner by a measuring and regulating device.

6. Apparatus for hemodialysis using a single needle, in which a predetermined volume of blood from a fistule, a vein or an artery is alternately drawn from the body of the patient by means of a pump to be filtered in an artificial kidney and then returned to the patient at the same puncture location, comprising:
- a needle,
- a section of tube between the needle and a pump,
- the artificial kidney,
- an expansion chamber composed of a closed receptacle provided with a blood delivery and removal tube and provided in its upper part with an apical air tube and provided, a few millimeters lower, with an infusion line enabling the kidney to be rinsed, medication to be administered and the height of the blood level to be adjusted by means of air under pressure, and
- a device for measuring and controlling the pump, wherein the pump is intermittently reversible and has an output directly connected to the artificial kidney, the needle, the pump and the expansion chamber are situated on a same blood line, the expansion chamber is farther from the puncture point than the pump, and the infusion line ends in the expansion chamber a few millimeters lower than the apical air tube.

7. The apparatus in accordance with claim 6, wherein the expansion chamber is provided with a single orifice or channel intended to deliver or return the blood.

8. The apparatus in accordance with claim 6, wherein the blood line, going from the puncture point, the pump and the artificial kidney, ends in the expansion chamber which is connected to a compliance chamber by a pressure line.

9. The apparatus in accordance with claims 6, 7 or 8, wherein the artificial kidney is connected on one side by means of a pump and a single needle or catheter to the circulatory system of the patient and is connected on the other side to an expansion chamber containing a receptacle provided with a blood delivery tube and a blood removal tube, and in its upper part an apical air tube intended to act as a pressure line and, a few millimeters lower, an infusion line for rinsing the kidney, administering medication and adjusting the level of the blood by means of the amount of air injected.

10. The apparatus in accordance with claim 9, wherein the expansion chamber and the compliance chamber contain a device for measuring pressure.

* * * * *